(12) United States Patent
Yang et al.

(10) Patent No.: US 11,739,319 B2
(45) Date of Patent: Aug. 29, 2023

(54) PCR PRIMER PAIR AND APPLICATION THEREOF

(71) Applicant: MGI TECH CO., LTD., Shenzhen (CN)

(72) Inventors: Lin Yang, Shenzhen (CN); Guodong Huang, Shenzhen (CN); Ya Gao, Shenzhen (CN); Yanyan Zhang, Shenzhen (CN); Haiping Zhang, Shenzhen (CN); Fang Chen, Shenzhen (CN); Haojun Jiang, Shenzhen (CN); Shaohong Zhang, Shenzhen (CN); Yuqian Wang, Shenzhen (CN); Yifan Xie, Shenzhen (CN); Hui Jiang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 622 days.

(21) Appl. No.: 16/624,779

(22) PCT Filed: Jun. 20, 2017

(86) PCT No.: PCT/CN2017/089196
§ 371 (c)(1),
(2) Date: Dec. 19, 2019

(87) PCT Pub. No.: WO2018/232595
PCT Pub. Date: Dec. 27, 2018

(65) Prior Publication Data
US 2020/0216838 A1    Jul. 9, 2020

(51) Int. Cl.
C12Q 1/68       (2018.01)
C12P 19/34      (2006.01)
C12N 15/10      (2006.01)
C12N 15/11      (2006.01)

(52) U.S. Cl.
CPC .......... *C12N 15/1093* (2013.01); *C12N 15/11* (2013.01)

(58) Field of Classification Search
CPC ............................ C12N 15/1093; C12N 15/11
See application file for complete search history.

(56) References Cited

U.S. PATENT DOCUMENTS

2006/0292611 A1    12/2006  Berka et al.
2009/0130720 A1    5/2009   Nelson et al.

FOREIGN PATENT DOCUMENTS

| CN | 101809170 A | 8/2010 |
| CN | 103820561 B | 4/2016 |
| EP | 2191011 A1  | 6/2010 |

OTHER PUBLICATIONS

New England Biolabs (NEB) catalog (1998/1999) pp. 121 and 284. (Year: 1998).*
Arne Skerra, "Phosphorothioate primers improve the amplification of DNA sequences by DNA polymerases with proofreading activity" Nucleic Acids Research, vol. 20, No. 14 3551-3554 (Year: 1992).*
Jurate Bitinaite, et al., "USER(tm) friendly DNA engineering and cloning method by uracil excision" Nucleic Acids Research, 2007, vol. 35, No. 6 (Year: 2007).*
Huanting Liu, et al., "An efficient one-step site-directed deletion, insertion, single and multiple-site plasmid mutagenesis protocol" BMC Biotechnology 2008, 8:91, pp. 1-10. (Year: 2008).*
Yan Yang, et al., "DNA Backbone Sulfur-Modification Expands Microbial Growth Range under Multiple Stresses by its antioxidation function" Nature—Scientific Reports; 7:3516, pp. 1-9 (Year: 2017).*
Hans E Krokan, et al., "Uracil in DNA—occurrence, consequences and repair" Oncogene (2002) 21, 8935-8948 (Year: 2002).*
Jeremy Pritchard, "Increase oligo stability with phosphorothioate modifications" from Integrated DNA Technologies, Support & Education, www.idtdna.com, Published Sep. 12, 2011. (Year: 2011).*
Małgorzata Boczkowska, "Stereodefined Phosphorothioate Analogues of DNA: Relative Thermodynamic Stability of the Model PS-DNA/DNA and PS-DNA/RNA Complexes" Biochemistry 2002, 41, 12483-12487 (Year: 2002).*
NEB Catalog (1998/1999) pp. 121 and 284 (Year: 1998).*
Printout of the information page for "Melting Temperature (Tm) Calculation" printed on Feb. 8, 2023 from http://www.biophp.org/minitools/melting_temperature, also including output for sequences related to instant Seq ID Nos. 4 and 37. (Year: 2023).*
Joséphine Sire, et al. "Uracil within DNA: an actor of antiviral immunity" Retrovirology 2008, 5:45 (Year: 2008).*
Zong, C. et al. "Genome-Wide Detection of Single Nucleotide and Copy Number Variations of a Single Human Cell", Science, 338(6114), Dec. 21, 2012 (Dec. 21, 2012), pp. 1622-1626.

(Continued)

*Primary Examiner* — Stephen T Kapushoc
(74) *Attorney, Agent, or Firm* — Westman, Champlin & Koehler, P.A.; Peter Sawicki; Amanda M. Prose

(57) ABSTRACT

Provided are a PCR primer pair and an application thereof. The PCR primer pair comprises: a first primer and a second primer, wherein the first primer comprises a first specific sequence and a first random sequence; the first specific sequence is located on end 3' of the first primer, and the first random sequence is located on end 5' of the first primer; the second primer comprises a second specific sequence and a second random sequence, the second specific sequence is located on end 3' of the second primer, and the second random sequence is located on end 5' of the second primer; moreover, the first specific sequence and the second specific sequence are an upstream primer and a downstream primer directed to a target sequence, respectively; the first random sequence and the second random sequence are reverse complementary; a predetermined restriction enzyme cutting site is connected between the first specific sequence and the first random sequence; and a predetermined restriction enzyme cutting site is connected between the second specific sequence and the second random sequence.

6 Claims, 4 Drawing Sheets
Specification includes a Sequence Listing.

(56) References Cited

OTHER PUBLICATIONS

International Search Report and Written Opinion issued for PCT/CN2017/089196, dated Mar. 22, 2018.
Search Report issued for EP patent application 17914886.1, dated Dec. 3, 2020.
Watson, D. E. et al. "Cloning and Assembly of PCR Products Using Modified Primers and DNA Repair Enzymes" (1997) Biotechniques, Informa Healthcare, vol. 23, No. 5.
Korfhage, C. "Clonal rolling circle amplification for on-chip DNA cluster generation" (2017) Biology Methods and Protocols, vol. 2, No. 1.

* cited by examiner

SEQUENCE LISTING

```
<160> NUMBER OF SEQ ID NOS: 38

<210> SEQ ID NO 1
<211> LENGTH: 40
<212> TYPE: DNA
<213> ORGANISM: Artificial
<220> FEATURE:
<223> OTHER INFORMATION: Primer

<400> SEQUENCE: 1 cccccccat ccccccccut tcttcgggtg ttgactttca                    40

<210> SEQ ID NO 2
<211> LENGTH: 40
<212> TYPE: DNA
<213> ORGANISM: Artificial
<220> FEATURE:
<223> OTHER INFORMATION: Primer

<400> SEQUENCE: 2 cccccccat gggcccggut tgacaatggt gtatctgggc                    40

<210> SEQ ID NO 3
<211> LENGTH: 42
<212> TYPE: DNA
<213> ORGANISM: Artificial
<220> FEATURE:
<223> OTHER INFORMATION: Primer

<400> SEQUENCE: 3 ccccccgat cggggcccut tcatccttac ttggatatgc cc                 42

<210> SEQ ID NO 4
<211> LENGTH: 44
<212> TYPE: DNA
<213> ORGANISM: Artificial
<220> FEATURE:
<223> OTHER INFORMATION: Primer

<400> SEQUENCE: 4
```

```
cccccccgcat ccggggggut cccttagaga acaaagtaaa aagc          44
```

<210> SEQ ID NO 5
<211> LENGTH: 44
<212> TYPE: DNA
<213> ORGANISM: Artificial
<220> FEATURE:
<223> OTHER INFORMATION: Primer

<400> SEQUENCE: 5

```
cccccccgctt gggccgcccut attgtgtttt tagagaagct caaa          44
```

<210> SEQ ID NO 6
<211> LENGTH: 42
<212> TYPE: DNA
<213> ORGANISM: Artificial
<220> FEATURE:
<223> OTHER INFORMATION: Primer

<400> SEQUENCE: 6

```
cccccccggtt cccgcggut caaagtgagc tctttgcctt tt          42
```

<210> SEQ ID NO 7
<211> LENGTH: 40
<212> TYPE: DNA
<213> ORGANISM: Artificial
<220> FEATURE:
<223> OTHER INFORMATION: Primer

<400> SEQUENCE: 7

```
cccccgcctt ccggcgccut tcaaggttga agcaaaagca          40
```

<210> SEQ ID NO 8
<211> LENGTH: 42
<212> TYPE: DNA
<213> ORGANISM: Artificial
<220> FEATURE:
<223> OTHER INFORMATION: Primer

<400> SEQUENCE: 8

```
cccccgcgat cccgccggut acatttcagc ttttgcaaac tt          42
```

<210> SEQ ID NO 9
<211> LENGTH: 40
<212> TYPE: DNA
<213> ORGANISM: Artificial
<220> FEATURE:
<223> OTHER INFORMATION: Primer

<400> SEQUENCE: 9

```
cccccgcgtt gcgcgggcut gggtcaaggg aactatccca          40
```

<210> SEQ ID NO 10
<211> LENGTH: 40
<212> TYPE: DNA
<213> ORGANISM: Artificial
<220> FEATURE:
<223> OTHER INFORMATION: Primer

<400> SEQUENCE: 10

```
cccccgggta ggccccggut ttggacacct tttcgtgtca          40
```

<210> SEQ ID NO 11
<211> LENGTH: 40
<212> TYPE: DNA
<213> ORGANISM: Artificial

```
<220> FEATURE:
<223> OTHER INFORMATION: Primer

<400> SEQUENCE: 11 ccccgcccttt cgcgcccgut gcctgctatt tgctttacca                              40

<210> SEQ ID NO 12
<211> LENGTH: 39
<212> TYPE: DNA
<213> ORGANISM: Artificial
<220> FEATURE:
<223> OTHER INFORMATION: Primer

<400> SEQUENCE: 12
ccccgccgtt gccgcgggut gtcatctgcc cccacagag                                39

<210> SEQ ID NO 13
<211> LENGTH: 40
<212> TYPE: DNA
<213> ORGANISM: Artificial
<220> FEATURE:
<223> OTHER INFORMATION: Primer

<400> SEQUENCE: 13
ccccggccta cggcccccut gtggagttcc actgcaaggt                               40

<210> SEQ ID NO 14
<211> LENGTH: 37
<212> TYPE: DNA
<213> ORGANISM: Artificial
<220> FEATURE:
<223> OTHER INFORMATION: Primer

<400> SEQUENCE: 14
ccccggcctt gcgcgccgut gtggaggctg acgaggc                                  37

<210> SEQ ID NO 15
<211> LENGTH: 40
<212> TYPE: DNA
<213> ORGANISM: Artificial
<220> FEATURE:
<223> OTHER INFORMATION: Primer

<400> SEQUENCE: 15
ccccggcctt ggcgggccut tgaagatgat cgggaaacac                               40

<210> SEQ ID NO 16
<211> LENGTH: 38
<212> TYPE: DNA
<213> ORGANISM: Artificial
<220> FEATURE:
<223> OTHER INFORMATION: Primer

<400> SEQUENCE: 16
ccccgggcta cccgccggut agtgcatcca cagggacc                                 38

<210> SEQ ID NO 17
<211> LENGTH: 40
<212> TYPE: DNA
<213> ORGANISM: Artificial
<220> FEATURE:
<223> OTHER INFORMATION: Primer

<400> SEQUENCE: 17
ccccggggat ccgcggccut gacgtgcaca acctcgacta                               40
```

<210> SEQ ID NO 18
<211> LENGTH: 38
<212> TYPE: DNA
<213> ORGANISM: Artificial
<220> FEATURE:
<223> OTHER INFORMATION: Primer

<400> SEQUENCE: 18
ccccggggtt ggggggggut gtgtttgccc acgacctg                               38

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19 gggggggat ggggggggut aatgagccct cagcctgc                                38

<210> SEQ ID NO 20
<211> LENGTH: 40
<212> TYPE: DNA
<213> ORGANISM: Artificial
<220> FEATURE:
<223> OTHER INFORMATION: Primer

<400> SEQUENCE: 20
ccgggcccat ggggggggut caccccaaat agtttgtgcc                             40

<210> SEQ ID NO 21
<211> LENGTH: 40
<212> TYPE: DNA
<213> ORGANISM: Artificial
<220> FEATURE:
<223> OTHER INFORMATION: Primer

<400> SEQUENCE: 21 gggcccgat cggggggut tgagcgcaat gagttcaata                               40

<210> SEQ ID NO 22
<211> LENGTH: 41
<212> TYPE: DNA
<213> ORGANISM: Artificial
<220> FEATURE:
<223> OTHER INFORMATION: Primer

<400> SEQUENCE: 22
ccccccggat gcggggggut tcctttctcc aaacagtgac c                           41

<210> SEQ ID NO 23
<211> LENGTH: 41
<212> TYPE: DNA
<213> ORGANISM: Artificial
<220> FEATURE:
<223> OTHER INFORMATION: Primer

<400> SEQUENCE: 23
ggcggcccaa gcggggggut gctcccaata ttacgcagtt c                           41

<210> SEQ ID NO 24
<211> LENGTH: 41
<212> TYPE: DNA
<213> ORGANISM: Artificial
<220> FEATURE:
<223> OTHER INFORMATION: Primer

```
<400> SEQUENCE: 24 ccgcgggaa ccgggggut catttctttt gcaggttgtc a                    41

<210> SEQ ID NO 25
<211> LENGTH: 41
<212> TYPE: DNA
<213> ORGANISM: Artificial
<220> FEATURE:
<223> OTHER INFORMATION: Primer

<400> SEQUENCE: 25
ggcgccggaa ggcgggggut catcctccta cggtgttgaa a                  41

<210> SEQ ID NO 26
<211> LENGTH: 40
<212> TYPE: DNA
<213> ORGANISM: Artificial
<220> FEATURE:
<223> OTHER INFORMATION: Primer

<400> SEQUENCE: 26
ccggcgggat cgcgggggut agatggcctg atggattctg                    40

<210> SEQ ID NO 27
<211> LENGTH: 42
<212> TYPE: DNA
<213> ORGANISM: Artificial
<220> FEATURE:
<223> OTHER INFORMATION: Primer

<400> SEQUENCE: 27
gcccgcgcaa cgcgggggut cacactaacg ttgtaatgcg ct                 42

<210> SEQ ID NO 28
<211> LENGTH: 40
<212> TYPE: DNA
<213> ORGANISM: Artificial
<220> FEATURE:
<223> OTHER INFORMATION: Primer

<400> SEQUENCE: 28
ccggggccta cccgggggut ggcactcaat aagggattgg                    40

<210> SEQ ID NO 29
<211> LENGTH: 42
<212> TYPE: DNA
<213> ORGANISM: Artificial
<220> FEATURE:
<223> OTHER INFORMATION: Primer

<400> SEQUENCE: 29
cgggcgcgaa gggcggggut gctgcttgta ttcacaccat tc                 42

<210> SEQ ID NO 30
<211> LENGTH: 37
<212> TYPE: DNA
<213> ORGANISM: Artificial
<220> FEATURE:
<223> OTHER INFORMATION: Primer

<400> SEQUENCE: 30
cccgcggcaa cggcggggut caccgccgtc tggttgg                       37

<210> SEQ ID NO 31
```

<211> LENGTH: 40
<212> TYPE: DNA
<213> ORGANISM: Artificial
<220> FEATURE:
<223> OTHER INFORMATION: Primer

<400> SEQUENCE: 31
gggggccgta ggccggggut gtgcttgagc cactggatgt                    40

<210> SEQ ID NO 32
<211> LENGTH: 37
<212> TYPE: DNA
<213> ORGANISM: Artificial
<220> FEATURE:
<223> OTHER INFORMATION: Primer

<400> SEQUENCE: 32
cggcgcgcaa ggccggggut ggcagagcgt cacagcc                       37

<210> SEQ ID NO 33
<211> LENGTH: 37
<212> TYPE: DNA
<213> ORGANISM: Artificial
<220> FEATURE:
<223> OTHER INFORMATION: Primer

<400> SEQUENCE: 33
ggcccgccaa ggccggggut cgccgctacc gcaccta                       37

<210> SEQ ID NO 34
<211> LENGTH: 40
<212> TYPE: DNA
<213> ORGANISM: Artificial
<220> FEATURE:
<223> OTHER INFORMATION: Primer

<400> SEQUENCE: 34
ccggcgggta gcccggggut tcttcatcac gttgtcctcg                    40

<210> SEQ ID NO 35
<211> LENGTH: 39
<212> TYPE: DNA
<213> ORGANISM: Artificial
<220> FEATURE:
<223> OTHER INFORMATION: Primer

<400> SEQUENCE: 35
ggccgcggat ccccggggut gtcctactgg catgacccc                     39

<210> SEQ ID NO 36
<211> LENGTH: 40
<212> TYPE: DNA
<213> ORGANISM: Artificial
<220> FEATURE:
<223> OTHER INFORMATION: Primer

<400> SEQUENCE: 36 cccccccccaa ccccggggut tagggacccc tcacattgtt                   40

<210> SEQ ID NO 37
<211> LENGTH: 59
<212> TYPE: DNA
<213> ORGANISM: Artificial
<220> FEATURE:
<223> OTHER INFORMATION: Forward universal primer

<400> SEQUENCE: 37

```
tgtgagccaa ggagttgaag tggcgcattg tcttcctaag accgcttggc ctccgactt      59

<210> SEQ ID NO 38
<211> LENGTH: 27
<212> TYPE: DNA
<213> ORGANISM: Artificial
<220> FEATURE:
<223> OTHER INFORMATION: Reverse universal primer

<400> SEQUENCE: 38
gaacgacatg gctacgatcc gacttgg                                         27
```

PCR PRIMER PAIR AND APPLICATION THEREOF

CROSS REFERENCE TO RELATED APPLICATIONS

This application is a US national phase application based upon PCT Application No. PCT/CN2017/089196 filed on Jun. 20, 2017, the entire content of which is incorporated herein by reference.

FIELD

The present disclosure relates to the field of biotechnology, in particular to PCR amplification, and more particular to PCR primer pair and application thereof.

BACKGROUND

Polymerase Chain Reaction (PCR) established by Mullis in 1983 has become a classical experimental method in molecular biology and related fields. Its application has been diversified, from gene amplification and gene detection, to gene cloning, genetic engineering, genetic analysis and the like, which even extends to non-biological areas. With the development in recent years, this technology itself has been improving, with continuously improved reliability. Meanwhile, a series of new concepts and experimental methods have been developed based on this basic principle of PCR, which has important application value in life science research.

Primers are one of the key factors in all PCR methods and technologies. Primer designs are currently available through computer and network. The advantages of online primer design include: 1) no need to be proficient in software operation; and 2) simultaneous analysis of many variables. However, good primers designed by conventional primer design software do not definitely produce good results in practical working, especially for template containing high GC regions and sequences similar to other target regions, thus ultimately resulting in poor specificity for the product amplified in the presence of the primers, as well as poor PCR amplification efficiency. In addition, the primers with optimization for these regions usually cannot get satisfactory results.

Therefore, the existing conventional PCR primer design method still needs to be improved.

SUMMARY

The present disclosure aims to at least solve one of the technical problems existing in the prior art. For this purpose, an object of the present disclosure is to propose a PCR primer design strategy and a corresponding PCR primer pair which can effectively reduce GC bias during PCR amplification and improve amplification specificity.

First, it should be noted that the present disclosure has been completed based on the following findings of present inventors.

There are various websites and software available online for free services of online primer design, such as NetPrimer (www.premierbiosoft.com). Lots of different primer design stand-alone software has been commonly used, with their own advantages. For example, Rightprimer™ (Bio2Disk), which has excellent proofreading function, can find out primers having highly strong specificity to sequences to be amplified in a short time by searching Genebank and aligning possible primers with background DNA. Oligo™ (Molecular Biology Insights, Inc.) is suitable for designing primers for Multiplex PCR and Consensus PCR, and can provide suitable PCR conditions. PrimerPremier (or Premierbiosoft) can design primers according to protein sequences in the case of unknown nucleic acid sequences, which can be especially useful in cloning new genes when only part of protein sequences are known. PrimerDesigner210 (Scientific and Educational Software) is widely used due to its small size and complete functionality.

However, good primers designed by conventional primer design software do not definitely produce good results in practical working, especially for template containing high GC regions and sequences similar to other target regions, thus ultimately resulting in poor specificity for the product amplified in the presence of the primers, as well as poor PCR amplification efficiency. In addition, the primers with optimization for these regions usually cannot get satisfactory results.

The present inventors after research have found that current PCR primers are required to be designed according to strict primer design conditions. PCR specificity and amplification efficiency greatly depend on the quality of primer designed, thus the primers generally cannot get good results in some repeat regions, high GC regions or regions with advanced structures, thereby plenty of labor and resources will cost for primer design and optimization. The present inventors have conducted a series of design and experimental explorations to solve the problems. Moreover, it is surprisingly discovered by the present inventors that such problems can be effectively addressed by addition of a pair of complementary sequences at the 5' ends of a conventional primer pair thus forming a primer pair with a stable primer-dimer structure which is reversely complementary at the 5' end and overhanging at the 3' end.

Further, the present inventors have also found that insertion of a predetermined restriction enzyme cutting site which is a sequence not comprised in a target sequence between the conventional primer and the complementary sequence, is capable of efficiently removing the conventional primer and the complementary sequence after PCR by cleaving the predetermined restriction enzyme cutting site of amplified products, thus facilitating subsequent library construction and purification.

Further, in a first aspect, the present disclosure in embodiments provides a PCR primer pair. In embodiments of the present disclosure, the PCR primer pair comprises a first primer and a second primer, wherein the first primer comprises a first specific sequence and a first random sequence, and the second primer comprises a second specific sequence and a second random sequence, wherein the first specific sequence is located at the 3' end of the first primer and the first random sequence is located at the 5' end of the first primer, the second specific sequence is located at the 3' end of the second primer and the second random sequence is located at the 5' end of the second primer, the first specific sequence and the second specific sequence are respectively an upstream primer and a downstream primer for a target sequence, the first random sequence and the second random sequence are reversely complementary, the first specific sequence is connected to the first random sequence via a first predetermined restriction enzyme cutting site, the second specific sequence is connected to the second random sequence via a second predetermined restriction enzyme cutting site, and the target sequence of the PCR primer pair does not comprise any predetermined restriction enzyme cutting site. The present inventors have surprisingly found that the PCR primer pair of the present disclosure can effectively reduce the GC bias during PCR amplification, thus increasing amplification specificity. Specifically, use of conventional primers will result in GC bias to some extent during PCR amplification of the next-generation sequencing library, but the PCR primer pair of the present disclosure (sometimes referred to as "Padlock Primer") is capable of effectively reducing the GC bias during library PCR amplification. Moreover, for the PCR primer pair of the present disclosure, insertion of a predetermined restriction enzyme cutting site which is a sequence not comprised in a target sequence between the conventional primer and the complementary sequence, is capable of efficiently removing the conventional primer and the complementary sequence after PCR by cleaving the predetermined restriction enzyme cutting site of amplified products, thus facilitating subsequent library construction and purification. Furthermore, the PCR primer pair of the present disclosure is particularly suitable for multiplex PCR amplification, that is, the PCR primer pairs of the present disclosure designed for a plurality of target sequences, can be effectively mixed, that is, for multiplex PCR.

In a second aspect, the present disclosure in embodiments provides a PCR amplification kit. In embodiments of the present disclosure, the kit comprises the PCR primer pair as described above. In embodiments of the present disclosure, using the kit comprising the PCR primer pair of the present disclosure for PCR amplification, can bring low GC bias, high amplification specificity and excellent amplification effect during amplification, compared to conventional primers. In addition, the PCR primer pair of the present disclosure is particularly suitable as a primer for multiplex PCR amplification.

In a third aspect, the present disclosure in embodiments provides a method for PCR amplification. In embodiments of the present disclosure, the method performs the PCR amplification by using the PCR primer pair or the PCR amplification kit as described above. Thus, PCR amplification of template can be effectively achieved through this method. Moreover, the method is capable of increasing specificity of PCR amplification, effectively reducing generation of non-specific products, and improving amplification efficiency.

In a fourth aspect, the present disclosure in embodiments provides a method for preparing a DNA library. In embodiments of the present disclosure, the method comprises the steps of:

(1) subjecting a DNA sample to be tested to first PCR amplification through the method for PCR amplification as described above, so as to obtain a first PCR amplification product comprising a loop-like substance, wherein the first specific sequence is connected to the first random sequence via a first predetermined restriction enzyme cutting site, the second specific sequence is connected to the second random sequence via a second predetermined restriction enzyme cutting site, the target sequence of the PCR primer pair does not comprise any predetermined restriction enzyme cutting site, the 5' end and the 3' end of the loop-like substance are not connected, and the 1-5$^{th}$ bases from each of the 5' end and the 3' end of the first primer of the PCR primer pair are respectively subjected to thio-modification, and the 1-5$^{th}$ bases from each of the 5' end and the 3' end of the second primer of the PCR primer pair are respectively subjected to thio-modification, and (2) subjecting the first PCR amplification product comprising the loop-like substance to cleavage by using an enzyme corresponding to the first and second predetermined restriction enzyme cutting sites, and preparing a library based on enzyme-cleaved products, so as to obtain a target DNA library.

In embodiments of the present disclosure, a linear DNA library or a circular DNA library can be efficiently prepared through the method. The obtained DNA library is of good library quality, which exhibits good effect for DNA preservation or library sequencing.

In embodiments of the present disclosure, the PCR primer pair of the present disclosure and use thereof have at least one of the following advantages:

1. The design strategy of the PCR primer pair of the present disclosure simplifies the primer design flow and optimizes the experimental steps. Each primer of the primer pair consists of a specific sequence at the 3' end and a random sequence (i.e. a complementary sequence) at the 5' end, thus the forward primer and the reverse primer form a stable dimer structure through complementary sequences, which does not need to meet strict conditions as conventional primers, thus greatly simplifying the design process. During conventional primer design, complementation of the 5' end and the 5' end of primers, generation of palindrome structure via primer itself and the like are necessarily to be avoided so as to ensure that no dimer structure is formed between primers and no self-extension of primers occurs for PCR. However, for designing the PCR primer pair of the present disclosure, such problems are not necessary to be considered, because the padlock primer is of a stable dimer structure, of which the 5' ends are complementary with each other and the 3' ends can complement with specific sequences and extend normally; in contrast, for a conventional primer pair, if its 5' ends are complementary with each other, its 3' ends will have no enough sequence to complement with specific sequences. Moreover, the complementary sequences at the 5' end formed between two primers of the padlock primer pair of the present disclosure display potential energy which is greatly stronger than that of self-palindrome structure, thus the dimer structure at the 5' end is preferably formed even the 5' end and the 3' end have sequences complementary with each other.

2. The PCR amplification method of the present disclosure can increase specificity of PCR amplification, thus effectively reducing generation of non-specific products. Starting from the second PCR cycle, bases at the 5' end of the primer (i.e. the random sequence) can reversely complement with bases at the 5' end of the newly-generated template, and the specific sequence at the 3' end of the primer can reversely complement with bases at the 3' end of the newly-generated template, that is, two recognition sites for binding between primer and template (refer to FIG. 3), thus significantly increasing binding ability between primer and template, and amplification specificity. Further, amplification efficiency is also effectively improved due to the increased binding ability.

3. Using the PCR primer pair of the present disclosure for PCR amplification can effectively reduce GC bias of different templates in amplification of sequencing libraries (especially, the next-generation sequencing library), because effective PCR amplification is only carried out after denaturation of template and binding of primer to template. The GC bias is generated because template containing some high GC regions would have renatured rapidly before the primer binds to the template during PCR, thus these high GC regions cannot be efficiently amplified. For the padlock primer of the present disclosure, two recognition sites for binding primer to template are presented, which can greatly improve the binding ability between primer and template, thereby the primer pair can be effectively paired with template containing high GC regions, thus reducing the GC bias.

4. For the PCR primer pair of the present disclosure, a predetermined restriction enzyme cutting site which is a sequence not comprised in a target sequence is inserted between the conventional primer (i.e. the specific sequence) and the complementary sequence (i.e. the random sequence), thus the conventional primer and the complementary sequence can be efficiently removed by cleaving the predetermined restriction enzyme cutting site of amplified products after PCR, thus facilitating subsequent library construction and purification. Since the target sequence does not include a uracil (U) base site cleaved by the USER enzyme, the predetermined restriction enzyme cutting site is designed to be the U base site cleaved by the USER enzyme accordingly, which can realize enzyme cleavage conveniently and efficiently.

Additional aspects and advantages of the present disclosure will be given in the following description partly, part of which will become apparent from the following description or be acknowledged through the practice of the present disclosure.

BRIEF DESCRIPTION OF THE DRAWINGS

The above and/or additional aspects and advantages of the present disclosure will become apparent and easily understood from the description of the embodiments in combination with the following drawings, in which.

DETAILED DESCRIPTION

Figure 1:
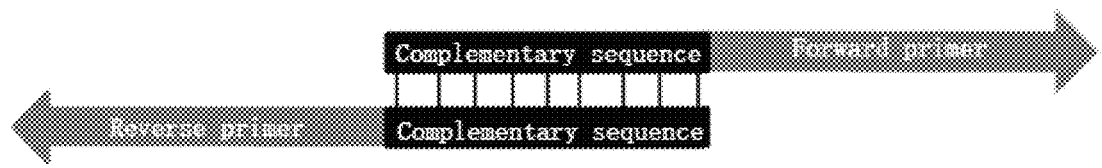
FIG. 1 is a schematic diagram showing the structure of a PCR primer pair (i.e. a padlock primer) of the present disclosure according to an embodiment of the present disclosure.
Figure 2:
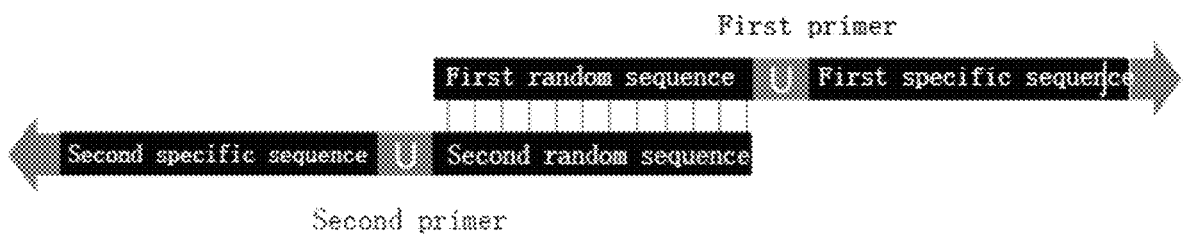
FIG. 2 is a schematic diagram showing the structure of a PCR primer pair (i.e. a padlock primer) of the present disclosure according to another embodiment of the present disclosure.

Embodiments of the present disclosure are described in detail below, examples of which are illustrated in the accompanying drawings. The embodiments described below with reference to the accompanying drawings are intended to be illustrative and for explanation of the present disclosure, which cannot be construed as limiting.

It should be noted, the terms "first" and "second" are used for purposes of description and are not intended to indicate or imply relative importance or significance or impliedly indicate quantity of the technical feature referred to. Thus, the feature defined with "first" and "second" may comprise one or more this feature either explicitly or implicitly. Further, in the description of the present disclosure, "a plurality of" means two or more than two, unless specified otherwise.

PCR Primer Pair

In a first aspect, the present disclosure in embodiments provides a PCR primer pair. According to embodiments of the present disclosure, the PCR primer pair comprises a first primer and a second primer, in which the first primer comprises a first specific sequence and a first random sequence, and the second primer comprises a second specific sequence and a second random sequence, in which the first specific sequence is located at the 3' end of the first primer and the first random sequence is located at the 5' end of the first primer, the second specific sequence is located at the 3' end of the second primer and the second random sequence is located at the 5' end of the second primer, the first specific sequence and the second specific sequence are respectively an upstream primer and a downstream primer for a target sequence, the first random sequence and the second random sequence are reversely complementary, the first specific sequence is connected to the first random sequence via a first predetermined restriction enzyme cutting site, the second specific sequence is connected to the second random sequence via a second predetermined restriction enzyme cutting site, and the target sequence of the PCR primer pair does not comprise any predetermined restriction enzyme cutting site. The present inventors have surprisingly found that the PCR primer pair of the present disclosure can effectively reduce the GC bias during PCR amplification, thus increasing amplification specificity. Specifically, use of conventional primers will result in GC bias to some extent during PCR amplification of the next-generation sequencing library, but the PCR primer pair of the present disclosure (sometimes referred to as "Padlock Primer") is capable of effectively reducing the GC bias during library PCR amplification. Moreover, for the PCR primer pair of the present disclosure, insertion of a predetermined restriction enzyme cutting site which is a sequence not comprised in a target sequence between the conventional primer and the complementary sequence, is capable of efficiently removing the conventional primer and the complementary sequence after PCR by cleaving the predetermined restriction enzyme cutting site of amplified products, thus facilitating subsequent library construction and purification. Furthermore, the enzyme-cleaved product is phosphorylated at the 5' end and has an overhang of Adenine (A) at the 3' end, which does not require additional end repair and can be directly used in adaptor ligation.

Further, the PCR primer pair of the present disclosure is particularly suitable for multiplex PCR amplification, that is, the PCR primer pairs of the present disclosure designed for a plurality of target sequences, can be effectively mixed, that is, for multiplex PCR. This is based on 1) extremely high specificity of the PCR primer pair of the present disclosure; and 2) different and unique complementary random sequences of individual primer pairs for different amplification regions and same complementary random sequences of primer pair for same amplification regions, thus avoiding mutual interference between primers that are used for different amplification regions, and contributing to inhibiting the production of non-specific products.

It should be noted that the "first random sequence" and the "second random sequence" of the present disclosure may be unfixed or fixed sequences as long as they are reversely complementary to each other.

According to embodiments of the present disclosure, the first specific sequence and the second specific sequence each have a TM value of 55-65° C., and the first primer and the second primer each have a TM value of 65-75° C. Thus, the PCR reaction is subjected to a first round of linear amplification under a low annealing temperature of 55-65° C., followed by a second round of circular amplification under a high annealing temperature of 65-72° C. in subsequent cycles. During the circular amplification, the specific sequence of primer cannot bind to the specific site of templates directly because the specific sequence has a TM value of 55-65° C. which is lower than the high annealing temperature of circular amplification. Such a circular amplification can be effectively performed only when the 5' end and the 3' end of the padlock primer bind to the 5' end and the specific site of templates respectively, i.e. performing the circular amplification through two recognition-site binding.

The PCR primer pair of the present disclosure is suitable for PCR amplification and library construction for any form of DNA sample to be tested. It should be noted that the "DNA sample to be tested" described in the present disclosure is somewhat different from the conventional understanding which does not include treated DNA. However, in the present disclosure, the "DNA sample to be tested" may include both treated DNA and untreated DNA. Generally, during construction of sequencing library, the genomic DNA of sample will be fragmented and added with adaptor for sequencing, thus obtaining DNA fragments carrying sequencing adaptors corresponding to a sequencing platform, which will be subjected to subsequent amplification and other steps for obtaining sequencing products. Such a DNA fragment carrying sequencing adaptor corresponding to a sequencing platform is called as the "treated DNA". Correspondingly, DNA fragments which are not treated according to the method as described above are called the "untreated DNA". If the PCR primer pair of the present disclosure is for untreated DNA, specific target fragments can be amplified; but if the PCR primer pair of the present disclosure is for treated DNA, whole genomic DNA fragments can be amplified.

According to some embodiments of the present disclosure, when the DNA sample to be tested is the treated DNA which carries a universal sequence, such as a sequencing adaptor, the first specific sequence and the second specific sequence have to specifically recognize a target sequence carrying the universal sequence accordingly, that is, the target sequence actually consists of a universal sequence and a target region sequence, in which the "universal sequence" herein means a sequence complement with the specific sequence of the PCR prime pair, including adaptor sequence for a sequencing platform, i.e. a sequencing adaptor. When the DNA sample to be tested is DNA fragments which do not carry a universal sequence, i.e. template for PCR reaction, the first specific sequence and the second specific sequence have to specifically recognize the target sequence accordingly. Meanwhile, if a sequencing library is required to be constructed, adaptor sequence for sequencing (i.e. a universal sequence) can be inserted into the random sequence or between the specific sequence and the random sequence for the first primer and the second primer respectively, so that PCR amplification products can be ligated with adaptors, thus can be effectively used in sequencing platforms.

According to further embodiments of the present disclosure, at least one of the first primer and the second primer further comprises a tag sequence, by which a plurality of samples can be subjected to PCR amplification simultaneously, and the samples can be distinguished by corresponding tag sequences. The position of the tag sequence in the first primer and the second primer is not particularly limited as long as the tag sequence can distinguish different samples without affecting PCR amplification. According to some specific examples of the present disclosure, the tag sequence may be located between a specific sequence and a random sequence, by which a first tag sequence may be arranged between the first specific sequence and the first random sequence of the first primer, and/or a second tag sequence may be arranged between the second specific sequence and the second random sequence of the second primer. According to another embodiment of the present disclosure, the tag sequence may also be arranged within the random sequence, i.e. forming a part of the random sequence, by which, exhibiting the function of distinguishing different samples without affecting PCR amplification as well.

According to embodiments of the present disclosure, the first random sequence and the second random sequence each have a length of 15-45 bp, and the first specific sequence and the second specific sequence each have a length of 15-30 bp.

According to embodiments of the present disclosure, the $1\text{-}5^{th}$ bases from each of the 5' end and the 3' end of the first primer are respectively subjected to modification, and the $1\text{-}5^{th}$ bases from each of the 5' end and the 3' end of the second primer are respectively subjected to modification, so as to effectively prevent from cleavage by exonuclease. According to some specific examples of the present disclosure, the $1\text{-}5^{th}$ bases from each of the 5' end and the 3' end of the first primer are respectively subjected to thio-modification, and the $1\text{-}5^{th}$ bases from each of the 5' end and the 3' end of the second primer are respectively subjected to thio-modification.

According to some embodiments of the present disclosure, the type of thio-modification is not particularly limited as long as the first primer and the second primer can be prevented from cleavage by exonuclease, such as cleavage by 5-3' exonuclease or 3-5' exonuclease. According to some specific examples of the present disclosure, the thio-modification is any one selected from phosphorothioate modification, methyl-sulfate modification and peptide nucleic acid modification.

According to an embodiment of the present disclosure, the first predetermined restriction enzyme cutting site and the second predetermined restriction enzyme cutting site each are a uracil (U) base site cleaved by the USER enzyme. Thus, since the target sequence does not include the U base site cleaved by the USER enzyme, it is possible to efficiently remove the conventional primer and the complementary sequence after PCR by cleaving the predetermined restriction enzyme cutting site of amplified products via the USER enzyme, thus facilitating subsequent library construction and purification.

In addition, it should be noted, referring to FIG. 1 which shows the schematic structure of the PCR primer pair of the present disclosure, the design strategy of the PCR primer pair of the present disclosure includes addition of a pair of complementary sequences at the 5'-ends of a conventional primer pair (including a forward primer and a reverse primer), thus forming a PCR primer pair (i.e. Padlock Primer, PP) which is reversely complementary at the 5' end and overhanging at the 3' end, in which two primers of the padlock primer pair form a stable primer-dimer structure, and the complementary sequences may be unfixed or fixed sequences. The first primer and the second primer of the PCR primer pair each have a length of 30-70 bp, and have a high TM value, generally of 65-75° C. The complementary sequences (i.e. the first random sequence and the second random sequence, being unfixed or fixed sequences) at the 5'-end of the padlock primer pair each have a length of 15-45 bp. The first specific sequence and the second specific sequence at the 3'-ends of the padlock primer pair, which are complementary to target sequences of a template, each have a length of 15-30 bp, and have a low TM value, generally of 55-65° C.

Figure 3:
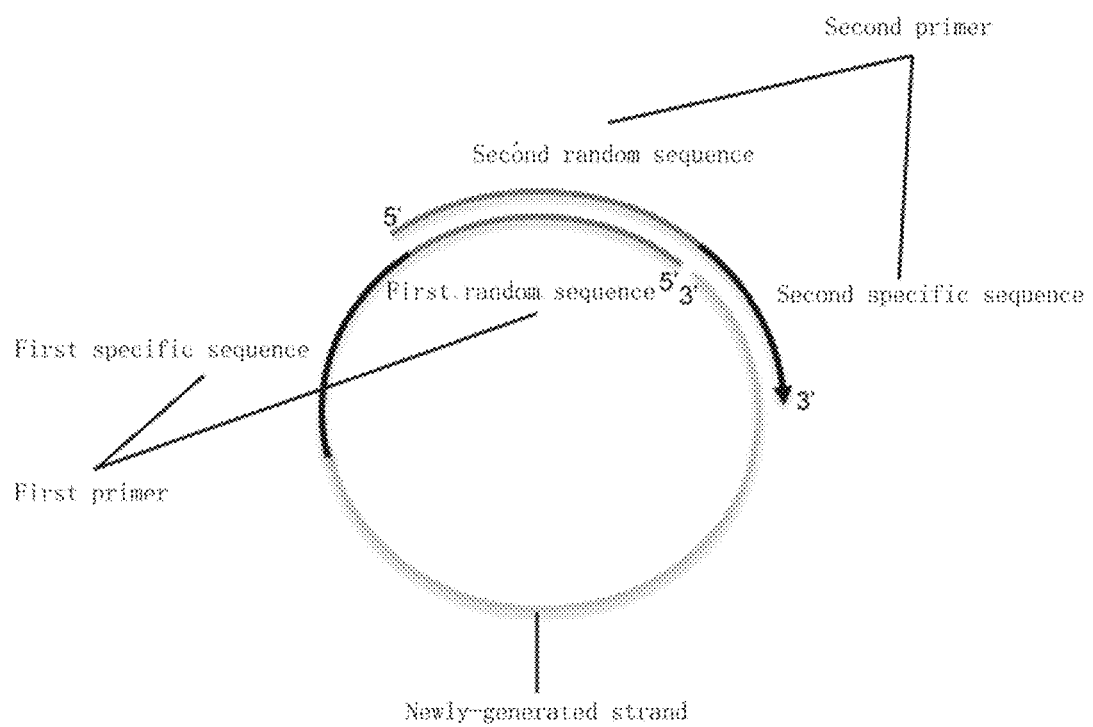
FIG. 3 is a schematic diagram showing binding between primer and newly-generated strand in the circular amplification of the present disclosure according to an embodiment of the present disclosure.

Further, for the application of the PCR primer pair of the present disclosure, the PCR primer pair of the present disclosure is subjected to two different amplification processes (i.e. two rounds of amplification) to complete the PCR amplification, referring to FIG. 3, in the first round of amplification, the annealing temperature is 55-65° C. and the cycle number is 1; and in the second round of amplification, the annealing temperature is 65-72° C. and the cycle number is 5-35. During the first round of amplification, only the specific sequence at the 3' end of the PCR primer pair can bind to template, thus the annealing temperature in this round is low. During the second round of amplification, the newly-generated template (i.e. the product of the first round of amplification) is firstly paired with the complementary sequence at the 5' end of the PCR primer pair (i.e. the first random sequence or the second random sequence), followed by pairing with the specific sequence at the 3' end (i.e. the first specific sequence or the second specific sequence), that is, two recognition sites for binding between primer and template, which greatly improved the annealing temperature of primer, resulting in a high annealing temperature.

Further, it should be noted, in the second round of amplification, the circular amplification can be effectively performed only when the 5' end and the 3' end of the primer bind to the newly-generated template simultaneously, thus specificity of PCR amplification and binding between primer and template are greatly improved via two recognition sites, with improved PCR amplification efficiency. Therefore, using the PCR primer pair of the present disclosure for PCR amplification, is capable of significantly increasing the specificity of PCR amplification, effectively reducing the generation of non-specific products, and reducing the GC bias during amplification, compared to conventional PCR primers. Thus, use of such a primer pair in sequencing, especially in the next-generation sequencing library, can effectively reduce the genome-wide GC bias in library enrichment and amplification.

Application

Further, in a second aspect, the present disclosure in embodiments also provides a PCR amplification kit. According to an embodiment of the present disclosure, the kit comprises the PCR primer pair as described above. According to an embodiment of the present disclosure, using the kit comprising the PCR primer pair of the present disclosure for PCR amplification, can bring low GC bias, high amplification specificity and excellent amplification effect during amplification, compared to conventional primers. In addition, the PCR primer pair of the present disclosure is particularly suitable as primers for multiplex PCR amplification.

Further, the present disclosure in embodiments proposes use of the PCR primer pair and the kit comprising the PCR primer pair.

In a third aspect, the present disclosure in embodiments provides a method for PCR amplification. According to an embodiment of the present disclosure, the method performs PCR amplification by using the PCR primer pair or the PCR amplification kit as described above. Thus, PCR amplification of template can be effectively achieved by using this method. Moreover, this method can increase specificity of PCR amplification, effectively reduce generation of non-specific products, and improve amplification efficiency.

According to an embodiment of the present disclosure, the method comprises two rounds of amplification. In the first round of amplification, the PCR primer pair and a template are subjected to linear amplification under an annealing temperature of 55-65° C., and in the second round of amplification, a product of the linear amplification is subjected to circular amplification under an annealing temperature of 65-72° C. Thus, starting from the second PCR cycle (i.e. circular amplification in the second round), bases at the 5' end of the first primer or the second primer can reversely complement with bases at the 5' end of the newly-generated template, and the specific sequence at the 3' end of the first primer or the second primer can reversely complement with bases at the 3' end of the newly-generated template, that is, two recognition sites for binding between primer and template (referring to FIG. 3), thus increasing specificity of PCR amplification, and effectively decreasing the generation of non-specific products.

According to an embodiment of the present disclosure, the two rounds of amplification are performed as the following amplification reaction procedure:

| | |
|---|---|
| step 1 | preheating for 2 minutes at 98° C. |
| step 2 | denaturing for 10 seconds at 98° C. |
| step 3 | annealing for 2 minutes at 55-65° C. |
| step 4 | amplifying for 30 seconds at 72° C. |
| step 5 | denaturing for 10 seconds at 98° C. |
| step 6 | annealing for 1 minute at 65-72° C. |
| step 7 | repeating steps 5 and 6 for 5-35 cycles |
| step 8 | extending for 5 minutes at 72° C. |

Therefore, the GC bias during PCR amplification is low, the amplification specificity is high and the amplification effect is excellent.

In a fourth aspect, the present disclosure in embodiments provides a method for preparing a circular DNA library.

In the fourth aspect, provided in embodiments is a method for preparing a DNA library. In embodiments, the method comprises the steps of:

(1) subjecting a DNA sample to be tested to first PCR amplification through the PCR amplification method as described above, so as to obtain a first PCR amplification product comprising a loop-like substance, in which the first specific sequence is connected to the first random sequence via a first predetermined restriction enzyme cutting site, the second specific sequence is connected to the second random sequence via a second predetermined restriction enzyme cutting site, the target sequence of the PCR primer pair does not comprise any predetermined restriction enzyme cutting site, the 5' end and the 3' end of the loop-like substance are not connected, and the 1-5$^{th}$ bases from each of the 5' end and the 3' end of the first primer of the PCR primer pair are respectively subjected to thio-modification, and the 1-5$^{th}$ bases from each of the 5' end and the 3' end of the second primer of the PCR primer pair are respectively subjected to thio-modification, and (2) subjecting the first PCR amplification product comprising the loop-like substance to cleavage by using an enzyme corresponding to the first and second predetermined restriction enzyme cutting sites, and preparing a library based on enzyme-cleaved products, so as to obtain a target DNA library.

According to embodiments of the present disclosure, a linear DNA library or a circular DNA library can be efficiently prepared through the method. The obtained DNA library has a good library quality, which exhibits good effect for DNA preservation or library sequencing.

According to an embodiment of the present disclosure, the first predetermined restriction enzyme cutting site and the second predetermined restriction enzyme cutting site each are a uracil (U) base site cleaved by the USER enzyme. Thus, since the target sequence does not include the U base site cleaved by the USER enzyme, it is possible to efficiently remove the conventional primer and the complementary sequence after PCR by cleaving the predetermined restriction enzyme cutting site of amplified products via the USER enzyme, thus facilitating subsequent library construction and purification.

According to an embodiment of the present disclosure, the step (2) is performed as follows:

subjecting the first PCR amplification product comprising the loop-like substance to enzymatic cleavage followed by terminal repairing and adenine (A) addition, so as to obtain an enzyme-cleaved product containing adenine (A) base at terminal;

ligating the enzyme-cleaved product containing A base at terminal with an adaptor, so as to obtain a ligation product, the ligation product being a linear DNA; and subjecting the ligation product to second PCR amplification, so as to obtain a second PCR amplification product, the second PCR amplification product constituting a linear DNA library, in which the second PCR amplification product is obtained by using a sequencing primer, and the sequencing primer is complementary to sequence of the adaptor.

Therefore, a linear DNA library can be effectively obtained, and the obtained library is of good quality.

According to some specific examples of the present disclosure, the enzymatic cleavage, the terminal repairing and the adenine (A) addition are performed by using the USER enzyme, T4 polynucleotide kinase, T4 DNA polymerase and Klenow fragment. Therefore, the enzymatic cleavage effect is good, and the obtained library is of good quality.

According to another embodiment of the present disclosure, the step (2) is performed as follows:

subjecting the first PCR amplification product comprising the loop-like substance to enzymatic cleavage, so as to obtain an enzyme-cleaved product containing the loop-like substance;

subjecting the enzyme-cleaved product containing the loop-like substance to a ligation reaction by using a ligase, such that the 5' end and the 3' end of the loop-like substance are ligated, thus forming a ligation product;

removing linear DNA from the ligation product, so as to obtain a circular DNA mixture; and subjecting the circular DNA mixture to third PCR amplification, so as to obtain a third PCR amplification product, the third PCR amplification product constituting a circular DNA library, in which in the third PCR amplification, the 3' end sequence of a forward primer is reversely complementary to the first random sequence, and the 3' end sequence of a reverse primer is reversely complementary to the second random sequence.

Therefore, a circular DNA library can be effectively obtained, and the obtained library is of good quality.

According to an embodiment of the present disclosure, the linear DNA is removed through a linear-chain digestion reaction.

According to an embodiment of the present disclosure, the method further comprises the step of purifying the circular DNA mixture prior to the third PCR amplification. Thus, the obtained library is of good quality.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang P T), *Molecular Cloning: A Laboratory Manual,* 3rd Ed., Science Press) or in accordance with the product instructions. If the manufacturers of reagents or instruments are not specified, the reagents or instruments may be conventional products that are commercially available, for example, from Illumina Company.

EXAMPLE 1: DETECTING WHETHER A FETUS SUFFERS FROM ACHONDROPLASIA (ACH) BY USING A PADLOCK PRIMER

1.1 Primer Design for Padlock Primer (i.e. PCR Primer Pair of the Present Disclosure, Referred to as "PP Primer" Below)

18 pairs of multiplex PCR primers containing all mutation sites of Achondroplasia were designed by using Primer 3, and such 18 primer pairs are all padlock primers, as shown in Table 1. The 3' end sequence of the padlock primer without any optimization has a TM value between 55° C. and 65° C. The 5' end complementary sequence which is unfixed has a TM value between 65° C. and 75° C. GC content of amplicon regions is between 26% and 75%, as shown in Table 2. The structure of padlock primer is shown in FIG. 1.

TABLE 1

Primer interval information

| Primer Nos. | Location | Amplicon Length | GC content |
|---|---|---|---|
| PP1 | chr8:5716321-5716432 | 100 | 26.0% |
| PP2 | chr12:86270815-86270910 | 96 | 31.3% |
| PP3 | chr11:17313443-17313562 | 120 | 31.7% |
| PP4 | chr4:180398777-180398891 | 115 | 32.2% |
| PP5 | chr2:125045070-125045149 | 80 | 32.5% |
| PP6 | chr9:31232026-31232095 | 70 | 32.9% |
| PP7 | chr13:31598809-31598908 | 100 | 33.0% |
| PP8 | chr6:135870701-135870815 | 115 | 33.9% |
| PP9 | chr10:26455826-26455900 | 75 | 38.7% |
| PP10 | chr13:67263837-67263896 | 60 | 41.7% |

TABLE 1-continued

Primer interval information

| Primer Nos. | Location | Amplicon Length | GC content |
|---|---|---|---|
| PP11 | chr13:43696242-43696306 | 65 | 46.2% |
| PP12 | chr4:1803633-1803692 | 60 | 58.3% |
| PP13 | chr4:1807776-1807838 | 63 | 58.7% |
| PP14 | chr4:1807337-1807414 | 78 | 59.0% |
| PP15 | chr4:1807862-1807947 | 86 | 64.0% |
| PP16 | chr4:1806071-1806170 | 100 | 64.0% |
| PP17 | chr4:1808930-1809025 | 96 | 68.8% |
| PP18 | chr4:1803545-1803620 | 76 | 75.0% |

Note:
PP: Padlock Primer; F: Forward primer; and R: Reverse primer

TABLE 2

Primer sequence information

| Primer Nos. | Sequence (5'-3', SEQ ID NO:) |
|---|---|
| PP1F | CCCCCCCCATCCCCCCCCUTTCTTCGGGTGTTGACTTTCA (1) |
| PP2F | CCCCCCCCATGGGCCCGGUTTGACAATGGTGTATCTGGGC (2) |
| PP3F | CCCCCCCGATCGGGGCCCUTTCATCCTTACTTGGATATGCCC (3) |
| PP4F | CCCCCCGCATCCGGGGGGUTCCCTTAGAGAACAAAGTAAAAAGC (4) |
| PP5F | CCCCCCGCTTGGGCCGCCUTATTGTGTTTTTAGAGAAGCTCAAA (5) |
| PP6F | CCCCCCGGTTCCCCGCGGUTCAAAGTGAGCTCTTTGCCTTTT (6) |
| PP7F | CCCCCGCCTTCCGGCGCCUTTCAAGGTTGAAGCAAAAGCA (7) |
| PP8F | CCCCCGCGATCCCGCCGGUTACATTTCAGCTTTTGCAAACTT (8) |
| PP9F | CCCCCGCGTTGCGCGGGCUTGGGTCAAGGGAACTATCCCA (9) |
| PP10F | CCCCCGGGTAGGCCCCGGUTTTGGACACCTTTTCGTGTCA (10) |
| PP11F | CCCCGCCCTTCGCGCCCGUTGCCTGCTATTTGCTTTACCA (11) |
| PP12F | CCCCGCCGTTGCCGCGGGUTGTCATCTGCCCCCACAGAG (12) |
| PP13F | CCCCGGCCTACGGCCCCUTGTGGAGTTCCACTGCAAGGT (13) |
| PP14F | CCCCGGCCTTGCGCGCCGUTGTGGAGGCTGACGAGGC (14) |
| PP15F | CCCCGGCCTTGGCGGGCCUTTGAAGATGATCGGGAAACAC (15) |
| PP16F | CCCCGGGCTACCCGCCGGUTAGTGCATCCACAGGGACC (16) |
| PP17F | CCCCGGGGATCCGCGGCCUTGACGTGCACAACCTCGACTA (17) |
| PP18F | CCCCGGGGTTGGGGGGGGUTGTGTTTGCCCACGACCTG (18) |
| PP1R | GGGGGGGGATGGGGGGGGUTAATGAGCCCTCAGCCTGC (19) |
| PP2R | CCGGGCCCATGGGGGGGGUTCACCCCAAATAGTTTGTGCC (20) |
| PP3R | GGGCCCCGATCGGGGGGGUTTGAGCGCAATGAGTTCAATA (21) |
| PP4R | CCCCCCGGATGCGGGGGGUTTCCTTTCTCCAAACAGTGACC (22) |
| PP5R | GGCGGCCCAAGCGGGGGGUTGCTCCCAATATTACGCAGTTC (23) |
| PP6R | CCGCGGGGAACCGGGGGGGUTCATTTCTTTTGCAGGTTGTCA (24) |
| PP7R | GGCGCCGGAAGGCGGGGGUTCATCCTCCTACGGTGTTGAAA (25) |
| PP8R | CCGGCGGGATCGCGGGGGUTAGATGGCCTGATGGATTCTG (26) |
| PP9R | GCCCGCGCAACGCGGGGGUTCACACTAACGTTGTAATGCGCT (27) |
| PP10R | CCGGGGCCTACCCGGGGGUTGGCACTCAATAAGGGATTGG (28) |
| PP11R | CGGGCGCGAAGGCGGGGUTGCTGCTTGTATTCACACCATTC (29) |
| PP12R | CCCGCGGCAACGGCGGGGUTCACCGCCGTCTGGTTGG (30) |

TABLE 2-continued

Primer sequence information

| Primer Nos. | Sequence (5'-3', SEQ ID NO:) |
| --- | --- |
| PP13R | GGGGGCCGTAGGCCGGGGUTGTGCTTGAGCCACTGGATGT (31) |
| PP14R | CGGCGCGCAAGGCCGGGGUTGGCAGAGCGTCACAGCC (32) |
| PP15R | GGCCCGCCAAGGCCGGGGUTCGCCGCTACCGCACCTA (33) |
| PP16R | CCGGCGGGTAGCCCGGGGUTTCTTCATCACGTTGTCCTCG (34) |
| PP17R | GGCCGCGGATCCCCGGGGUTGTCCTACTGGCATGACCCC (35) |
| PP18R | CCCCCCCCAACCCCGGGGUTTAGGGACCCCTCACATTGTT (36) |

Note:
PP refers to Padlock Primer; F refers to Forward primer; R refers to Reverse primer; predetermined restriction enzyme cutting site is the U base site cleaved by the USER enzyme; and each primer consists of 18 bp of random sequence, 1 bp of U base and a specific sequence from 5' end to 3' end.

1.2 Experimental Steps

In this experiment, 10 cases of pregnant women's plasma were selected, including 5 cases of ACH-positive samples and 5 cases of ACH-negative samples. The experiment was conducted in duplicate.

1.2.1 Extraction of Cell-Free DNA

Figure 4:
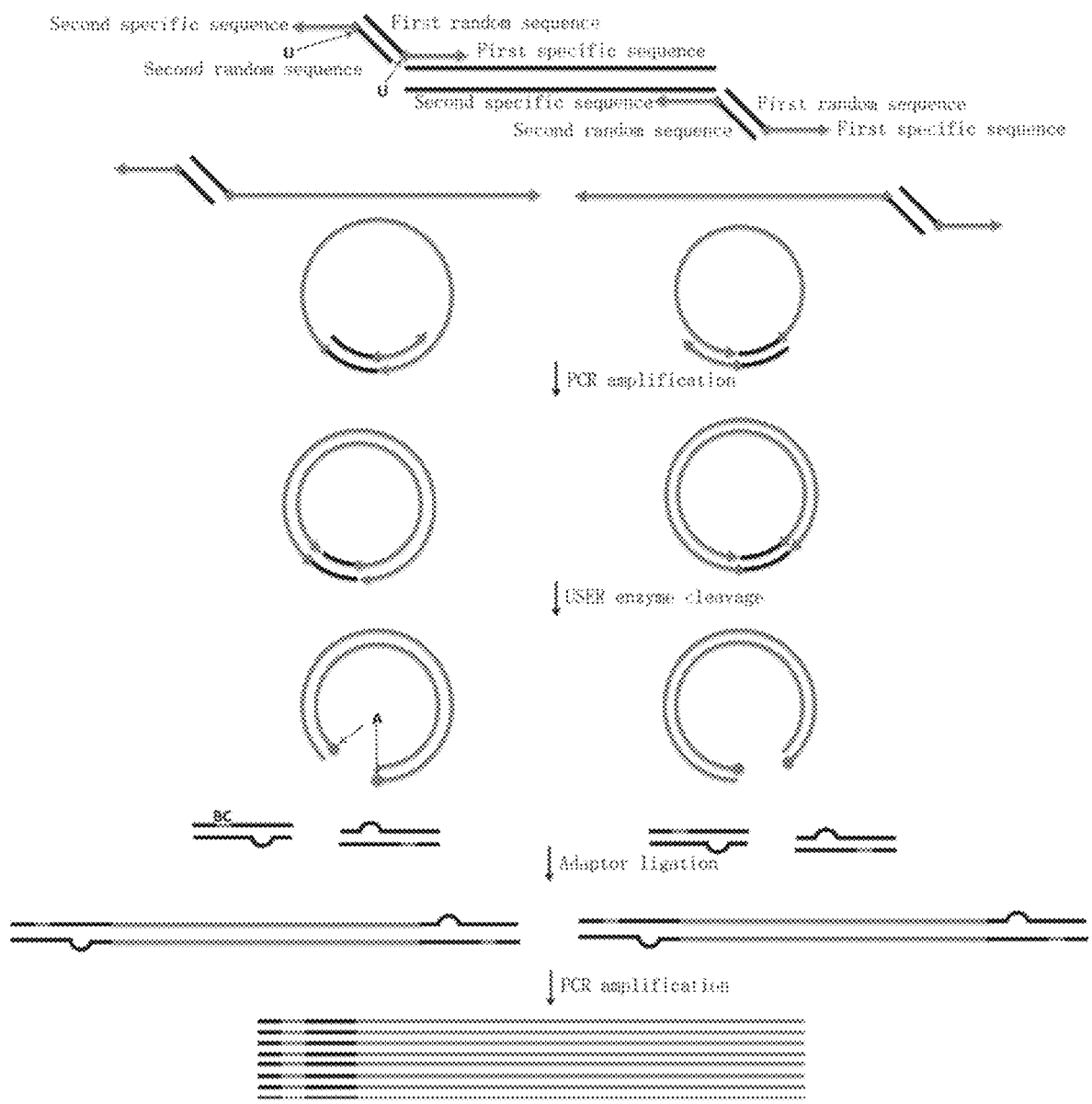
FIG. 4 is a schematic flow chart showing preparation of a linear library by using the PCR primer pair of the present disclosure according to an embodiment of the present disclosure.

200 μL of plasma taken from respective ACH-positive samples and ACH-negative samples was extracted for DNA by using Magen beads, with products dissolved in 17 μL of TE, for use. Target libraries were prepared through the following steps, specifically referring to FIG. 4 showing the schematic flow chart of library preparation.

1.2.2 Multiplex PCR Amplification

The extracted cfDNA from each sample were subjected to multiplex PCR amplification according to the amplification system shown in the following table:

| | |
| --- | --- |
| rTaq Buffer (10X) | 2 μL |
| cfDNA | 16.3 μL |
| Forward and reverse primer pool | 1 μL |
| dNTP Mixture | 0.5 μL |
| rTaq DNA Polymerase | 0.2 μL |
| Total | 20 μL |

Note:
The forward and reverse primer pool was a mixture of all corresponding primers in Table 2 in an equal proportion.

The amplification conditions for multiplex PCR amplification were as follows:

| | |
| --- | --- |
| step 1 | 98° C., 2 minutes |
| step 2 | 98° C., 10 seconds |
| step 3 | 58° C., 2 minutes |
| step 4 | 72° C., 30 seconds |
| step 5 | 98° C., 10 seconds |
| step 6 | 68° C., 1 minute |
| step 7 | repeating steps 5 and 6 for 25 cycles |
| step 8 | 72° C., 5 minutes |

The amplified products of samples each were purified with 1.8 times of volumes of Axygen beads, followed by dissolving in 37 μL of TE, for use.

1.2.3 Library Preparation

The purified products of samples obtained in step 1.2.2 were respectively subjected to USER enzyme cleavage followed by terminal repairing, adenine (A) addition, adaptor ligation and PCR amplification as below.

1) Reaction system of USER enzyme cleavage, terminal repairing and adenine (A) addition

| | |
| --- | --- |
| 10X PNK buffer | 5 μL |
| dNTP mix (2.5 mM) | 1 μL |
| dATP (10 mM) | 2 μL |
| T4 PNK | 1 μL |
| USER | 2 μL |
| Bsm | 1 μL |
| T4 Ploymerase | 0.5 μL |
| Klenow Fragment | 0.5 μL |
| DNA | 37 μL |
| Total | 50 μL |

The reaction procedure of USER enzyme cleavage, terminal repairing and adenine (A) addition was reaction at 20° C. for 30 minutes and at 65° C. for another 30 minutes.

2) Reaction system of adaptor ligation

| | |
| --- | --- |
| Previous DNA | 50 μL |
| 10X PNK buffer | 2 μL |
| PEG 4000 (50%) | 7.5 μL |
| Adaptor (100 μM) | 0.5 μL |
| T4 DNA Ligase | 2 μL |
| Water | 3 μL |
| Total | 65 μL |

The reaction procedure of adaptor ligation was reaction at 25° C. for 15 minutes and at 4° C. for another 10 minutes.

The resulting products were purified with 1.2 times of volumes of Axygen beads, followed by dissolving in 21 μL of TE, for use.

3) PCR amplification

The ligation products of samples obtained in the previous step each were subjected to PCR amplification according to the amplification system shown in the following table:

| | |
|---|---|
| Kappa HIFI premixed mixture (2X) | 25 μL |
| Ligation product | 21 μL |
| Forward universal primer | 2 μL |
| Reverse universal primer | 2 μL |
| Total | 50 μL |

The forward universal primer is of a sequence from 5' end to 3' end (5'-3'):

(SEQ ID NO: 37)
TGTGAGCCAAGGAGTTGAAGTGGCGCATTGTCTTCCTAAGACCGCTTGG
CCTCCGACTT.

The reverse universal primer is of a sequence from 5' end to 3' end (5'-3'):

(SEQ ID NO: 38)
GAACGACATGGCTACGATCCGACTTGG.

The PCR amplification procedure was as follows:

| | |
|---|---|
| Step 1 | 98° C., 2 minutes |
| Step 2 | 98° C., 15 seconds |
| Step 3 | 56° C., 15 seconds |
| Step 4 | 72° C., 30 seconds |
| Step 5 | repeating steps 2-4 for 10 cycles |
| Step 6 | 72° C., 5 minutes |

The resulting products were purified with 1.2 times of volumes of Axygen beads, followed by dissolving in 21 μL of TE, thus obtaining a target library, which was subsequently subjected to fragment analysis by 2100 Bioanalyzer and qubit quantification, results shown in FIG. 5 and Table 3.

Figure 5:
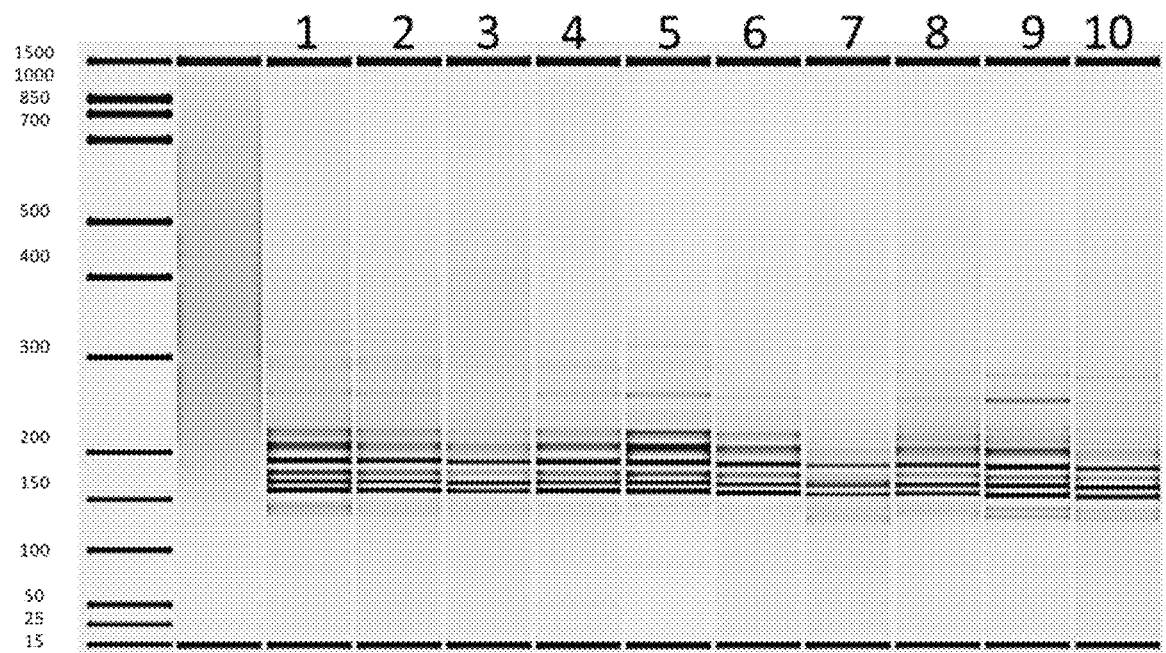
FIG. 5 is a graph showing results of fragment analysis and qubit quantitative detection of target libraries of various samples obtained in Example 1.

As seen in FIG. 5, samples 1-5 are positive samples, and samples 6-10 are negative samples.

TABLE 3

Experimental starting amount and library output

| Samples | Input Plasma (μL) | Lib Output (ng) |
|---|---|---|
| Sample 1 | 200 | 497 |
| Sample 2 | 200 | 479 |
| Sample 3 | 200 | 434 |
| Sample 4 | 200 | 427 |
| Sample 5 | 200 | 488 |
| Sample 6 | 200 | 304 |
| Sample 7 | 200 | 466 |
| Sample 8 | 200 | 343 |
| Sample 9 | 200 | 491 |
| Sample 10 | 200 | 306 |

1.2.4 On-Machine Sequencing

The qualified library was subjected to on-machine sequencing by using BGISEQ-500 sequencing platform and the sequencing type of PE50BP.

1.2.5 Data Analysis

The obtained sequencing results were subjected to data analysis, specifically including: filtering off-machine sequencing reads, such that the reads having base quality less than 10 were removed, thus ensuring high quality for the data used for base frequency analysis; aligning the filtered clean reads to the human genome reference sequence HG19 (GRCH37) through alignment software bwa (V0. 7.7-r441); calculating coverage depth of 4 bases (ATCG) at sites to be detected based on the alignment results, and thus obtaining information such as most-likely mutation site and frequency thereof, sequencing error and frequency thereof and the like via the coverage depth; performing GC bias correction according to GC distribution in regions (where the mutation site and primer were presented), as well as the likely frequency of sequencing error; and detecting the mutation sites obtained as above by using the mutation detection tool GATK (V3.6) which is most accurate currently; and filtering and annotating through the corresponding mutation database.

Figure 6:
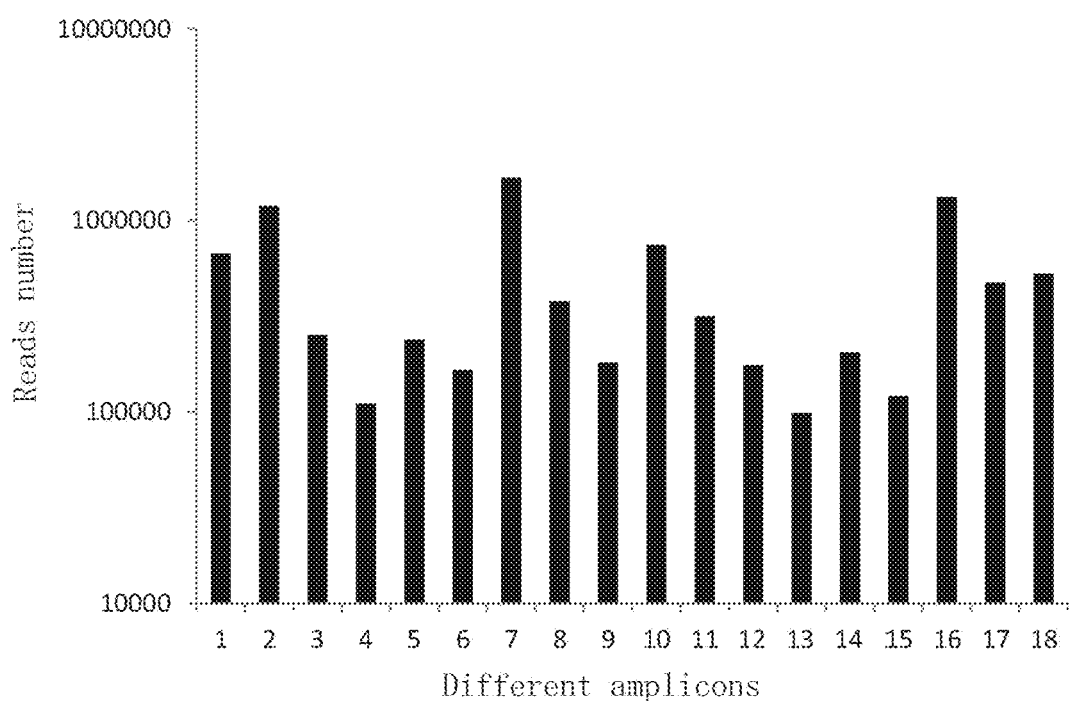
FIG. 6 is a graph showing statistic results (i.e. uniformity detection results) of sequencing reads of different amplicon in target libraries of various samples obtained in Example 1.
Figure 7:
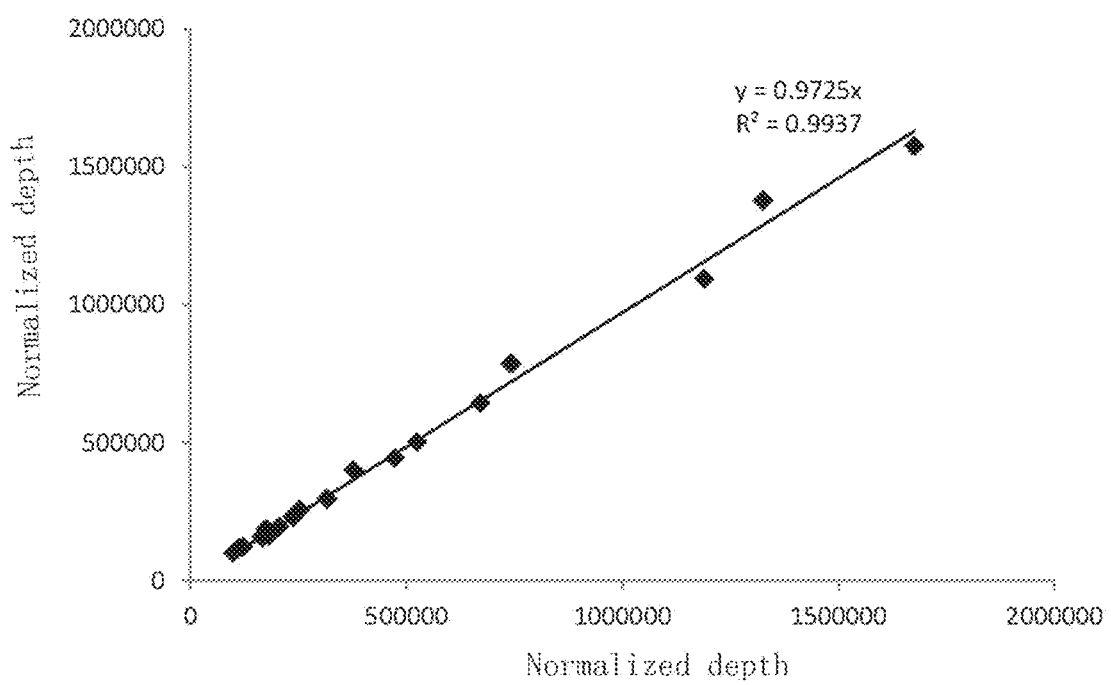
FIG. 7 is a graph showing comparison results (i.e. stability detection results) of depth at a same position in two experiments in Example 1.

As a result, the present inventors have found that it is possible to accurately detect mutations as low as 1% by using the PCR primer pair of the present disclosure for multiplex PCR amplification and library construction. Specifically, 5 positive samples in the 10 samples were all detected to be positive, respectively with the mutation frequency of 5.3%, 7.2%, 3.5%, 5.6% and 6.2%; and 5 negative samples in the 10 samples were all detected to be negative, respectively with the mutation frequency of 0.3%, 0.1%, 0.2%, 0.2% and 0.1%, refer to Table 5. Moreover, the method of the present disclosure displays good specificity, with between 90% and 94% of alignment rate, and between 92% and 95% of capture efficiency; is of 100% of coverage (refer to Table 4); is of good uniformity, obtaining 0.1× average depth greater than 94% (refer to Table 4 and FIG. 6); and has good stability, as well as few differences between different samples (refer to FIG. 7).

TABLE 4

PE50 + 10 off-machine data

| Samples | Original data | Alignment rate | Capture efficiency | Coverage | Uniformity* |
|---|---|---|---|---|---|
| Sample 1 | 8345502 | 91.2% | 94.6% | 100% | 94.7% |
| Sample 2 | 11127336 | 91.8% | 92.5% | 100% | 94.7% |
| Sample 3 | 8856963 | 91.5% | 92.8% | 100% | 94.7% |
| Sample 4 | 10252352 | 90.9% | 94.4% | 100% | 94.7% |
| Sample 5 | 10569812 | 94.4% | 94.6% | 100% | 94.7% |
| Sample 6 | 12563987 | 91.0% | 94.3% | 100% | 94.7% |
| Sample 7 | 11127336 | 92.2% | 94.7% | 100% | 94.7% |
| Sample 8 | 10200058 | 93.1% | 92.3% | 100% | 94.7% |
| Sample 9 | 9565862 | 92.8% | 91.2% | 100% | 94.7% |
| Sample 10 | 9282202 | 90.1% | 93.2% | 100% | 94.7% |

*Uniformity: rate of the number of amplicon of which depth is greater than 0.1 X mean depth (18/19 = 94.7%).

TABLE 5

Accuracy of mutation detection

| Samples | Location | Mutation type | Detection ratio |
|---|---|---|---|
| Sample 1 | Chr4 1806119 | G > A | 5.3% |
| Sample 2 | Chr4 1806119 | G > A | 7.2% |
| Sample 3 | Chr4 1806119 | G > A | 3.5% |
| Sample 4 | Chr4 1806119 | G > A | 5.6% |
| Sample 5 | Chr4 1806119 | G > A | 6.2% |
| Sample 6 | Chr4 1806119 | G > A | 0.3% |
| Sample 7 | Chr4 1806119 | G > A | 0.1% |

TABLE 5-continued

Accuracy of mutation detection

| Samples | Location | Mutation type | Detection ratio |
|---|---|---|---|
| Sample 8 | Chr4 1806119 | G > A | 0.2% |
| Sample 9 | Chr4 1806119 | G > A | 0.2% |
| Sample 10 | Chr4 1806119 | G > A | 0.1% |

In addition, the present inventors also performed a series of experiments, and have discovered that the PCR primer pair of the present disclosure is useful not only for cfDNA samples, but also widely for samples like genomic DNA, FFPE, urine DNA, fresh frozen sample and the like; and can be applied for constructing both BGI-SEQ library and other libraries for platform, such as illumina and proton.

INDUSTRIAL APPLICABILITY

The PCR primer pair of the present disclosure can be effectively used for PCR amplification of DNA samples to be tested, effectively reduce GC bias during PCR amplification, and improve amplification specificity. Such a PCR primer pair is particularly suitable for multiplex PCR amplification.

Although specific embodiments of the present disclosure have been described in detail, it would be appreciated by those skilled in the art that various modifications and alternatives of the details can be made according to teachings of the present disclosure, which are all within the scope of the present disclosure. The full scope of the present disclosure is given by the appended claims and any equivalents thereof.

Reference throughout this specification to terms "an embodiment", "some embodiments", "illustrative embodiment", "an example", "a specific example" or "some examples" means that a particular feature, structure, material, or characteristic described in connection with the embodiment or example is included in at least one embodiment or example of the present disclosure. Thus, the description with reference to the terms "an embodiment", "some embodiments", "illustrative embodiment", "an example", "a specific example" or "some examples" throughout this specification are not necessarily referring to the same embodiment or example of the present disclosure. Furthermore, the particular features, structures, materials, or characteristics may be combined in any suitable manner in one or more embodiments or examples.

What is claimed is:

1. A PCR primer pair, comprising a first primer and a second primer, wherein
the first primer comprises a first specific sequence and a first random sequence, and
the second primer comprises a second specific sequence and a second random sequence, wherein
the first specific sequence is located at the 3' end of the first primer and the first random sequence is located at the 5' end of the first primer,
the second specific sequence is located at the 3' end of the second primer and the second random sequence is located at the 5' end of the second primer,
the first specific sequence and the second specific sequence are respectively an upstream primer and a downstream primer for a target sequence,
the first random sequence and the second random sequence are reversely complementary,
the first specific sequence is connected to the first random sequence via a first predetermined restriction enzyme cutting site,
the second specific sequence is connected to the second random sequence via a second predetermined restriction enzyme cutting site, and
the target sequence of the PCR primer pair does not comprise any predetermined restriction enzyme cutting site,
wherein the first random sequence and the second random sequence each have a length of 15-45 bp, and
the first specific sequence and the second specific sequence each have a length of 15-30 bp,
wherein the first predetermined restriction enzyme cutting site and the second predetermined restriction enzyme cutting site each are a uracil (U) base site.

2. The PCR primer pair according to claim 1, wherein the $1^{st}$-$5^{th}$ bases from each of the 5' end and the 3' end of the first primer respectively have thio-modification, and
the $1^{st}$-$5^{th}$ bases from each of the 5' end and the 3' end of the second primer respectively have thio-modification.

3. The PCR primer pair according to claim 2, wherein the thio-modification is selected from phosphorothioate modification and methyl-sulfate modification.

4. The PCR primer pair according to claim 1, wherein the first primer has a sequence as shown in SEQ ID NO.: 1-18, and the second primer has a sequence as shown in SEQ ID NO.: 19-36.

5. The PCR primer pair according to claim 1, wherein the first primer and the second primer each have a length of 30-70 bp.

6. The PCR primer pair according to claim 1, wherein the $1^{st}$-$5^{th}$ bases from each of the 5' end and the 3' end of the first primer respectively have a peptide nucleic acid modification.

* * * * *